United States Patent
Chiou et al.

(10) Patent No.: US 11,819,559 B2
(45) Date of Patent: Nov. 21, 2023

(54) COSMETIC COMPOSITIONS COMPRISING AN ANTIMICROBIAL SYSTEM WITH REDUCED EYE IRRITATION OR DISCOMFORT

(71) Applicant: L'OREAL, Paris (FR)

(72) Inventors: Catherine Chiou, Saddle Brook, NJ (US); Ryuji Hara, Springfield, NJ (US)

(73) Assignee: L'OREAL, Paris (FR)

( * ) Notice: Subject to any disclaimer, the term of this patent is extended or adjusted under 35 U.S.C. 154(b) by 32 days.

(21) Appl. No.: 17/039,393

(22) Filed: Sep. 30, 2020

(65) Prior Publication Data
US 2022/0096345 A1  Mar. 31, 2022

(51) Int. Cl.
| | |
|---|---|
| *A61K 8/34* | (2006.01) |
| *A61K 8/02* | (2006.01) |
| *A61K 8/06* | (2006.01) |
| *A61K 8/41* | (2006.01) |
| *A61K 8/49* | (2006.01) |
| *A61Q 1/14* | (2006.01) |

(52) U.S. Cl.
CPC ............ *A61K 8/347* (2013.01); *A61K 8/0208* (2013.01); *A61K 8/062* (2013.01); *A61K 8/064* (2013.01); *A61K 8/345* (2013.01); *A61K 8/41* (2013.01); *A61K 8/4926* (2013.01); *A61Q 1/14* (2013.01); *A61K 2800/30* (2013.01); *A61K 2800/48* (2013.01)

(58) Field of Classification Search
None
See application file for complete search history.

(56) References Cited

U.S. PATENT DOCUMENTS

| | | | | |
|---|---|---|---|---|
| 2014/0348886 A1* | 11/2014 | Johnson | ............... | A61Q 5/00 424/401 |
| 2015/0017218 A1* | 1/2015 | Pettigrew | ............ | A61K 8/36 424/409 |
| 2016/0000670 A1* | 1/2016 | Pesaro | ............... | A61K 8/37 424/59 |
| 2021/0038485 A1* | 2/2021 | Robinson | ............ | A61K 8/8129 |

FOREIGN PATENT DOCUMENTS

| | | |
|---|---|---|
| CN | 107 349 162 A | 11/2017 |
| CN | 110 664 633 A | 1/2020 |
| CN | 111 388 365 A | 7/2020 |
| DE | 10 2009 022444 A1 | 1/2010 |
| DE | 10 2016 205580 A1 | 10/2017 |
| EP | 3 494 850 A1 | 6/2019 |
| WO | 2021026248 A1 | 2/2021 |

OTHER PUBLICATIONS

Search Report issued to French counterpart Application No. FR2012222 dated Sep. 6, 2021.
'PCT Notification of Transmittal of the International Search Report and the Written Opinion of the International Searching Authority, or the Declaration issued to counterpart Application No. PCT/US2021/052787 dated Jan. 12, 2022.

* cited by examiner

*Primary Examiner* — Kyung S Chang
(74) *Attorney, Agent, or Firm* — McNees Wallace & Nurick LLC

(57) ABSTRACT

A cosmetic composition includes an antimicrobial system that includes an antimicrobial agent comprising 4-hydroxyacetophenone and one or more additional antimicrobial agents comprising piroctone olamine. The antimicrobial system can be used in a cosmetic composition wherein the composition is a makeup removal composition that is one of an O/W emulsion, a W/O emulsion, a micellar water, a makeup removing wipe, or a two-phase (or multi-phase) composition. The antimicrobial system may be free or essentially free of any one or more of parabens, alcohols, formaldehyde, and formaldehyde-derived compounds. In some particular embodiments, the composition is free or essentially free of parabens, formaldehyde, formaldehyde-derived compounds, pentylene glycol, phenoxyethanol, hexylglycerin, ethylhexylglycerin, octylglycerin, benzylglycerin, 3-heptoyl-2,2-propandiol, and 1,2-hexandiol.

20 Claims, No Drawings

COSMETIC COMPOSITIONS COMPRISING AN ANTIMICROBIAL SYSTEM WITH REDUCED EYE IRRITATION OR DISCOMFORT

FIELD

This invention relates to makeup removal and cleansing compositions that comprise a novel antimicrobial system that provide makeup removal efficacy with minimal irritation to eyes and other tissue.

BACKGROUND

Typically, makeup removal products and cleansers are used on the entire face, including some which are necessarily used around the eyes. Indeed, there are cosmetic cleansers designed specifically for removal of stubborn makeup such as regular or waterproof mascara, eye liner, eye shadow, glitters, and long-wear foundation, in addition to longer-lasting lip products. Such cleansers can require repeated tugging and rubbing on the skin, in particular on and around delicate eye tissues, which can be inherently irritating to the skin. In addition, most makeup removing products include antimicrobial and preservative agents that may also give rise to stinging and burning sensation in the eye area as a result of proximity to and in some cases incidental contact with eyes during the makeup removing process.

Accordingly, there is a need for cosmetic compositions, in particular cleansers and cleansing wipe articles that will provide makeup removal and have the benefits of preservation and protection from microbial growth without causing eye irritation. These compositions and articles would desirably exclude antimicrobial, preservative and cleansing components that are irritants, such as, pentylene glycol, phenoxyethanol, and parabens, without compromising cleansing and antimicrobial efficacy.

According to the instant disclosure, a new antimicrobial system, when used in a makeup removing or cleaning composition, unexpectedly produces significantly reduced or no eye irritation as compared with similarly formulated compositions that include conventional antimicrobial systems.

SUMMARY

The disclosure provides, in various embodiments, a cosmetic composition, comprising:
  i. an antimicrobial system that comprises:
    a) an antimicrobial agent comprising 4-hydroxyacetophenone; and
    b) at least one additional antimicrobial agent comprising piroctone olamine.

In accordance with the various embodiments, the cosmetic composition that includes antimicrobial system is one of an O/W emulsion, a W/O emulsion, a micellar water, a wipe, or a two-phase (or multi-phase) composition. In some particular embodiments, the cosmetic composition is a makeup removing composition that is one of an O/W emulsion, a W/O emulsion, a micellar water, a makeup removing wipe, or a two-phase (or multi-phase) composition.

In some embodiments, the at least one additional antimicrobial agent may also include any one or more of the following antimicrobial agents and their salts, including caprylyl glycol, caprylhydroxamic acid, chlorphenesin, benzoic acid, salicylic acid, benzyl alcohol, phenethyl alcohol, and benzalkonium chloride.

In some embodiments, the cosmetic composition is free or essentially free of any one or more of parabens, alcohols, formaldehyde, and formaldehyde-derived compounds. In some particular embodiments, the composition is free or essentially free of parabens, formaldehyde, and formaldehyde-derived compounds.

In some particular embodiments, the composition is free or essentially free of alcohols comprising one or more of ethanol and isopropyl alcohol.

In some embodiments, the composition is free or essentially free of antimicrobials that comprise any one or more of, pentylene glycol, phenoxyethanol, hexyl glycerin, ethylhexylglycerin, octylglycerin, benzylglycerin, 3-heptoyl-2, 2-propandiol, and 1,2-hexandiol.

In accordance with the various embodiments, the antimicrobial agent comprising 4-hydroxyacetophenone is present from about 0.2% to about 1% by weight of the composition; the at least one additional antimicrobial agent comprising piroctone olamine (Octopirox), when present, is present from about 0.05% to about 1.5% by weight of the composition. In some particular embodiments, the composition comprises 4-hydroxyacetophenone present from about 0.25% to about 2% by weight of the composition; the at least one additional antimicrobial agent comprising piroctone olamine, when present, is present from about 0.05% to about 1.5% by weight of the composition.

In accordance with some embodiments, the disclosure provides a makeup removal composition, comprising:
  i. an antimicrobial system that comprises:
    a) an antimicrobial agent comprising 4-hydroxyacetophenone; and
    b) at least one additional antimicrobial agent comprising piroctone olamine; and
  ii. a water-based cleansing system.

In accordance with some embodiments, the disclosure provides a makeup removal composition comprising:
  i. an antimicrobial system that comprises:
    a) an antimicrobial agent comprising 4-hydroxyacetophenone; and
    b) at least one additional antimicrobial agent comprising piroctone olamine; and
  ii. a water-based cleansing system that comprises:
    a) one or more lipophilic emollients;
    b) at least one thickener for a water-based system;
    c) one or more humectants; and
    d) water.

In accordance with some embodiments:
  i. the at least one lipophilic emollient is selected from isohexadecane, C15-19 alkane, isododecane, undecane, tridecane, Isopropyl myristate, dicaprylyl ether, ethylhexyl palmitate, Isopropyl palmitate, cetearyl ethylhexanoate, Isononyl isononanoate, isopropyl isostearate, diisopropyl sebacate, coco caprylate/caprate, diisopropyl adipate, and combinations thereof;
  ii. the at least one thickener is selected from acrylates/C10-30 alkyl acrylate crosspolymer, sodium acrylates copolymer, carbomer, xanthan gum, hydroxypropyl guar, *Ceratonia siliqua* (carob) gum, ammonium polyacryloyldimethyl taurate, ammonium acryloyldimethyltaurate/steareth-25 methacrylate crosspolymer, and polyacrylate crosspolymer-6 and combinations thereof;
  iii. the at least one humectant comprises glycerin.

In various embodiments, the compositions may include more than one of each of the components, and may further include one or more additives selected from fragrances, pearlescent agents, silica, proteins, protein hydrolysates, vitamins, panthenol, silicones, odor absorbers and coloring materials; essential oils; fruit extracts, for example *Pyrus Malus* (Apple) Fruit Extract, and Aloe Barbadensis Leaf Juice Powder; citric acid, sodium chloride; neutralizing or pH-adjusting agents (e.g., triethylamine (TEA) and sodium hydroxide); and combinations thereof.

In some embodiments, a cosmetic article comprising the cosmetic composition is provided, the article comprising:
a. a water-insoluble substrate comprising a cosmetic wipe;
b. Impregnated in the water-insoluble substrate a cosmetic composition according to the disclosure,
wherein the cosmetic composition is impregnated onto the water-insoluble substrate in a soaking rate of 250% to 400% by weight of the cleansing composition to the weight of the substrate.

In accordance with the various embodiments, the article is formed from synthetic materials or formed from natural biodegradable and sustainably sourced natural originated fiber, natural fiber, or regenerated or recycled natural fiber.

In some particular embodiments, the article comprises nonwoven fibers, the fibers formed from natural biodegradable and sustainably sourced fibers selected from (1) natural originated fiber comprising one or a combination of pulp, viscose, lyocell, cellulose acetate, and cotton, (2) natural fiber comprising one or a combination of hemp, flax, seaweed, ramie, banana, and pineapple, and (3) regenerated or recycled fiber comprising cotton, and combinations of these.

In some embodiments, the disclosure provides a cosmetic composition, comprising: an antimicrobial system that comprises: an antimicrobial agent comprising 4-hydroxyacetophenone; and at least one additional antimicrobial agent comprising piroctone olamine; and a skin care system selected from: a bi-phase water-based cleansing system; a multi-phase water-based cleansing system; a single-phased micellar water water-based cleansing system; and a topical composition that is one of a serum, essence, cream or mask.

These and other aspects of the invention are set out in the appended claims and described in greater detail in the detailed description of the invention.

This disclosure describes exemplary embodiments in accordance with the general inventive concepts and is not intended to limit the scope of the invention in any way. Indeed, the invention as described in the specification is broader than and unlimited by the exemplary embodiments set forth herein, and the terms used herein have their full ordinary meaning.

It is to be understood that both the foregoing general description and the following detailed description are exemplary and explanatory only and are not restrictive of the disclosure.

DETAILED DESCRIPTION

The term "article" is understood here to mean the combination composed of a water-insoluble support and a composition impregnated on the support. This article can in particular be a wipe but it can also have any form including those described below. The water-insoluble substrate is absorbent and sufficiently strong not to disintegrate during the use thereof. The use of the article as defined above for caring for the skin or hair and/or cleaning and/or removing makeup from and/or scrubbing the skin.

"Keratinous substrate" and "keratinous tissue" each includes but is not limited to skin, hair, and nails.

"Cosmetically acceptable" means a carrier that is compatible with any keratinous substrate.

In various embodiments, the disclosure provides an antimicrobial system and a makeup removal composition that includes the antimicrobial system. The antimicrobial system includes an antimicrobial agent comprising 4-hydroxyacetophenone and one or more additional antimicrobial agents comprising piroctone olamine. In some examples, the antimicrobial system can be used in a skin care system selected from: a bi-phase water-based cleansing system; a multi-phase water-based cleansing system; a single-phased micellar water water-based cleansing system; and a topical composition that is one of a serum, essence, cream or mask. In some particular examples, the antimicrobial system can be used in makeup removal compositions that are one of an O/W emulsion, a W/O emulsion, a micellar water, or a two-phase (or multi-phase) composition. In some embodiments, the composition is used in a makeup removing wipe.

In various embodiments, the antimicrobial system may be free or essentially free of any one or more of parabens, alcohols, formaldehyde, and formaldehyde-derived compounds. In some particular embodiments, the composition is free or essentially free of parabens, formaldehyde, and formaldehyde-derived compounds. In some particular embodiments, the composition is free or essentially free of one or more of pentylene glycol, phenoxyethanol, hexyl glycerin, ethylhexylglycerin, octylglycerin, benzylglycerin, 1,3-propanediol, 3-heptoyl-2,2-propanediol, and 1,2-hexandiol. In some particular embodiments, the composition is free or essentially free of each of, pentylene glycol, phenoxyethanol, hexyl glycerin, ethylhexylglycerin, octylglycerin, benzylglycerin, 1,3-propanediol, 3-heptoyl-2,2-propandiol, and 1,2-hexandiol. In some embodiments, the composition is free or essentially free of all alcohols. In some particular embodiments, the composition is free or essentially free of alcohols comprising one or more of ethanol and isopropyl alcohol.

In various embodiments, the compositions may include more than one of each of the components, and may further include one or more additives including humectants, preservatives, fragrances, actives, and pH adjusters, among other cosmetically acceptable additives.

Through consumer evaluations of MUR efficacy, compositions according to the disclosure demonstrated makeup removal performance consistent with comparative compositions and significantly improved performance with respect to eye irritation.

In some embodiments, the disclosure provides the antimicrobial system and the makeup removal composition imbued into a cosmetic application article. The article may be formed of synthetic materials, such as PET (Polyethylene terephthalate, or polyester) and PP (polypropylene), which may be used alone or in combination with natural-based material. And in some embodiments, the article may be formed of sustainable and biodegradable substrates from sources such as (1) natural originated fiber based nonwovens, such as pulp, viscose, lyocell, cellulose acetate, cotton, (2) natural fiber based nonwovens, such as hemp, flax, seaweed, ramie, banana, pineapple, and (3) regenerated or recycled fiber based nonwovens, such as cotton.

Many conventional cosmetic articles, such as wipes, are formed of fossil-based polymeric materials, such as PET (Polyethylene terephthalate, or polyester) and PP (polypropylene), which may be used alone or in combination with natural-based material. Such synthetic substrates are desirable because they are relatively less costly to produce and deliver good tensile strength, however, because they essentially never degrade, they contribute adversely to the environment. With increasing focus in the cosmetics industry on sustainability, there is a need for cosmetic articles that employ solid substrates to draw from sources such as (1) natural originated fiber based nonwovens, such as pulp, viscose, lyocell, cellulose acetate, cotton, (2) natural fiber based nonwovens, such as hemp, flax, seaweed, ramie, banana, pineapple, and (3) regenerated or recycled fiber based nonwovens, such as cotton. As used herein, the terms "natural originated fiber" refers to fiber materials that are formed by chemical processing that render derivatives based on natural fibers; "natural fiber" means non-derivative forms of natural fibers; and "regenerated/recycled" means natural fibers that are reclaimed from goods formed with such fibers.

In some embodiments, the article herein is formed of substrates that are obtained from sustainable sources and are biodegradable. In some particular embodiments, these materials are selected from natural originated fiber formed into nonwovens, using fibers such as pulp, viscose, lyocell, cellulose acetate, and cotton. And in certain embodiments, the substrates used to form cosmetic articles are nonwovens of lyocell. According to those embodiments that include natural biodegradable and sustainably sourced fibers, a clear benefit realized is the opportunity to reduce the environmental burden. Other benefits may also be achieved using sustainable and biodegradable substrates. As further described herein, articles that employ sustainable and biodegradable substrates, particularly lyocell nonwovens, demonstrate certain mechanical, textural, and absorbent properties.

An article according to the disclosure is moist to the touch. It exhibits the advantage of being comfortable during application to the skin and having a nourishing effect due to the presence of an oily phase. When it is used for cleaning or removing makeup from the skin, an article according to the disclosure is passed over the skin, while possibly leaving it applied for a time sufficient for the makeup products to be dissolved in the impregnating composition of the article, and then the skin is wiped. The skin can also optionally be rinsed subsequently. The article according to the invention is preferably a cosmetic article appropriate for caring for and/or treating the skin of the face, body or hands and for cleaning or removing makeup from the skin of the face and/or body. It can also be used for caring for the hair and for removing makeup from the eyes.

An article according to the disclosure can have any form appropriate to the desired objective. It can constitute a wipe that has a generally rectangular, square or other shape that may be single ply, multiple ply, and may be folded or un-folded. The article can also be in the form of a glove, of a mitten or in any other form appropriate for practical use on the face or the body, for example in the form of a face with holes for the sites of the eyes, nose and/or mouth, or in the form of a makeup-removing fingerstall for application in removing makeup from the eyelashes, or in the form of a single- or double-sided disc which can in particular comprise two sides impregnated with different compositions. The article can also comprise a rough surface which makes possible the exfoliation (scrubbing) of the skin.

In an exemplary embodiment, compositions that comprise an inventive antimicrobial system according to the disclosure may be in the form of a makeup removal composition comprising one or more lipophilic emollients, one or more volatile silicone compounds, at least one thickener for a water-based system and one or more humectants and water. It will be appreciated, of course, that in other embodiments, the inventive antimicrobial system according to the disclosure may be provided in a composition that is generally in the form of one of an O/W emulsion, a W/O emulsion, a micellar water, a makeup removing wipe, or a two-phase (or multi-phase) composition. Thus, according to the teachings in the art with respect to selection of ingredients for various cosmetic compositions, and in particular for makeup removing compositions, the antimicrobial system may be incorporated to replace the conventional antimicrobial systems in the art. And in particular, such compositions are free or essentially free of any one or more of parabens, surfactants, alcohols, formaldehyde, and formaldehyde-derived compounds. And in some embodiments, the compositions are free or essentially free of antimicrobials comprising any one or more of, pentylene glycol, phenoxyethanol, hexyl glycerin, ethylhexylglycerin, octylglycerin, benzylglycerin, 3-heptoyl-2,2-propandiol, and 1,2-hexanediol.

Lipophilic Emollient

In accordance with the disclosure, compositions according to the disclosure can include one or more lipophilic emollients.

Lipophilic emollients may be selected from branched or linear, liquid alkane with carbon chain length of C11 to C20. In various embodiments, liquid alkanes may be selected from those with a carbon chain length of from C11 to C20. The liquid alkanes may be selected from those with a carbon chain length of from C11 to C20, or from C15 to C19, or one of C11, C12, C13, C14, C15, C16, C17, C18 to C19. In some particular embodiments, suitable liquid alkanes that may be used according to the disclosure include hydrocarbon-based oils containing from 8 to 16 carbon atoms, and especially branched C8-C16 alkanes such as C8-C16 isoalkanes. In some exemplary embodiments, such liquid alkanes may be chosen from isoparaffins, for instance isododecane (also known as 2,2,4,4,6-pentamethylheptane), isodecane, and isohexadecane.

In some embodiments, the at least one lipophilic emollient comprises one or more of isohexadecane, C15-19 alkane, isododecane, undecane, tridecane and combinations thereof. In some embodiments, the at least one lipophilic emollient comprises isohexadecane.

Lipophilic emollients may be selected from polar emollients. Emollients are oil-phase ingredients selected from esters, triglycerides, ethers, carbonates, alcohols, oils, butters, fatty acids, and their combinations thereof. In various embodiments, the polar emollients may be selected from those with a molecular weight of 400 g/mol or less. More, generally, the polar emollient may have a molecular weight in the range from about 50 g/mol to about 350 g/mol.

In some embodiments, suitable polar emollients that may be used according to the disclosure include those derived from C12-C50 fatty acids, preferably C16-C22 saturated fatty acids, and monohydric alcohols. In some embodiments, such esters may be chosen from isopropyl myristate, methyl palmitate, isopropyl laurate, isopropyl palmitate, ethylhexyl palmitate, ethylhexyl laurate, ethylhexyl oleate, ethylhexyl isononanoate, myristyl myristate, 2-ethylhexyl caprate/caprylate (or octyl caprate/caprylate), 2-ethylhexyl palmitate, isostearyl neopentanoate, isononyl isononanoate, hexyl laurate, esters of lactic acid and of fatty alcohols comprising 12 or 13 carbon atoms, dicaprylyl carbonate and their mixtures.

In some embodiments, the at least one lipophilic emollient comprises one of isopropyl myristate, dicaprylyl ether, ethylhexyl palmitate, isopropyl palmitate, cetearyl ethylhexanoate, isononyl isononanoate, isopropyl isostearate, diisopropyl sebacate, coco caprylate/caprate, diisopropyl adipate, and combinations thereof. In some particular embodiments the at least one lipophilic emollient comprises isopropyl myristate.

In some embodiments the at least one lipophilic emollient comprises dimethicone, cyclopentasiloxane, and/or other silicone emollients.

In some particular embodiments the at least one lipophilic emollient comprises each of isohexadecane, isopropyl myristate, dimethicone, cyclopentasiloxane, and/or other silicone emollients.

The amount of each of the at least one or more lipophilic emollients that may be present in the composition are provided in a range of from about 1% to about 12% by weight, or from about 3% to about 11% by weight, or from about 5% to about 10% or any suitable combination, sub-combination, range, or sub-range thereof by weight, based on the weight of the composition. One of ordinary skill in the art, however, will appreciate that other ranges are within the scope of the invention.

Thus, each of at least one or more lipophilic emollients in the composition may be present by weight, based on the total weight of the composition, from about 1, 2, 3, 4, 5, 6, 7, 8, 9, 10, 11 to about 12 percent, including increments and ranges therein and there between.

Thickener

In accordance with the disclosure, compositions according to the disclosure can include at least one thickener.

In some embodiments, the at least one thickener may be selected from one or more of natural gums and synthetic polymers, for example starches (corn, rice, tapioca, potato), gums (xanthan carrageenan, gellan, *sclerotium*). In some particular embodiments, the at least one thickener may be selected from acrylates/C10-30 alkyl acrylate crosspolymer, Sodium Acrylates Copolymer, carbomer, xanthan gum, hydroxypropyl guar, *Ceratonia siliqua* (carob) gum, ammonium polyacryloyldimethyl taurate, ammonium acryloyldimethyltaurate/steareth-25 methacrylate crosspolymer, and polyacrylate crosspolymer-6.

In some embodiments the composition comprises two or more thickeners. In some such embodiments, the composition comprises one or both of the polymeric thickeners acrylates/C10-30 alkyl acrylate crosspolymer and sodium acrylates copolymer, and optionally one or more additional polymeric thickeners.

The amount of each of the at least one thickener is present in the composition in a range of from about 0.01% to about 5%, or from about 0.01% to about 3%, or from about 0.05% to about 2.5%, or any suitable combination, sub-combination, range, or sub-range thereof by weight, based on the weight of the composition. One of ordinary skill in the art, however, will appreciate that other ranges are within the scope of the invention.

In some embodiments, the total amount of thickener in the composition is present from about 0.01% to about 5%, or from about 1.0% to about 3%, or from about 2% to about 2.55%, or any suitable combination, sub-combination, range, or sub-range thereof by weight, based on the weight of the composition. One of ordinary skill in the art, however, will appreciate that other ranges are within the scope of the invention.

Thus, one or more thickener, when present, is present by weight, based on the total weight of the composition, from about 0.01, 0.02, 0.03, 0.04, 0.05, 0.06, 0.07, 0.08, 0.09, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.5, 4.0, 4.5 to about 5.0 percent, including increments and ranges therein and there between.

Solvent/Water

In accordance with the various embodiments, water is present in the compositions in a range from about 40% to about 90%, or from about 55% to about 85%, or from about 60% to about 75%, or from about 65% to about 70%, or any suitable combination, sub-combination, range, or sub-range thereof by weight, based on the weight of the composition. One of ordinary skill in the art, however, will appreciate that other ranges are within the scope of the invention. Thus, water is present, by weight, based on the total weight of the composition, from about 40, 45, 50, 55, 60, 65, 70, 75, 80, 85, to about 90 weight percent, including increments and ranges therein and there between The water used may be sterile demineralized water and/or a floral water such as rose water, cornflower water, chamomile water or lime water, and/or a natural thermal or mineral water such as, for example: water from Vittel, water from the Vichy basin, water from Uriage, water from La Roche Posay, water from La Bourboule, water from Enghien-les-Bains, water from Saint Gervais-les-Bains, water from Neris-les-Bains, water from Allevar-les-Bains, water from Digne, water from Maizieres, water from Neyrac-les-Bains, water from Lons-le-Saunier, water from Eaux Bonnes, water from Rochefort, water from Saint Christau, water from Les Fumades, water from Tercis-les-Bains or water from Avene. The water phase may also comprise reconstituted thermal water, that is to say a water comprising trace elements such as zinc, copper, magnesium, etc., reconstituting the characteristics of a thermal water.

The pH of the composition is not limited but is generally between 2 and 12, and in some embodiments, is one of between 3 and 11, and between 5 and 9, and between 6 and 8, and in some embodiments is 7. The pH can be adjusted to the desired value by addition of a base (organic or inorganic) to the composition, for example ammonia or a primary, secondary or tertiary (poly)amine, such as monoethanolamine, diethanolamine, triethanolamine, isopropanolamine or 1,3-propanediamine, or alternatively by addition of an inorganic or organic acid, advantageously a carboxylic acid, such as, for example, citric acid.

In some embodiments, the composition can include one or more additional solvents, for example, monoalcohols such as monohydric $C_1$-$C_8$ alcohols such as ethanol, propanol, butanol, isopropanol, isobutanol, and benzyl alcohol, and phenylethyl alcohol.

In some embodiments, the composition is free or essentially free of any and all alcohols. In some particular embodiments, the composition is free or essentially free of alcohols comprising one or more of ethanol and isopropyl alcohol.

Humectant/Hydrating Agent

In accordance with the disclosure, one more humectants may be present in the compositions. In some embodiments, the humectant may comprise one or more of polyols, including, for example, glycerin, glycerol, butylene glycol, propylene glycol, isoprene glycol, dipropylene glycol, hexylene glycol and polyethylene glycols, monoethylene glycol, diethylene glycol, triethylene glycol, diethylene glycol, hexylene glycol, glycol ethers such as monopropylene, dipropylene and tripropylene glycol alkyl(C1-C4)ethers, squalane, triacetin, sugars, such as glucose, xylitol, maltitol, sorbitol, sucrose pentaerythritol, inositol, pyrrolidone carboxylic acid, lactic acid, lithium chloride, acetamide MEA, sodium lactate, urea, dicyanamide, hyaluronic acid, aloe vera, honey, and seaweed extract.

In some embodiments, the compositions include a humectant comprising glycerin.

In accordance with the various embodiments, the amount of humectant present in the compositions can range from about 1% to about 15%, or from about 2% to about 12%, or from about 3% to about 7%, or from about 4% to about 5%, or any suitable combination, sub-combination, range, or sub-range thereof by weight, based on the weight of the composition. One of ordinary skill in the art, however, will appreciate that other ranges are within the scope of the invention.

Thus, any one of or a combination of humectant may be present, by weight, based on the total weight of the composition, is from about 1, 2, 3, 4, 5, 6, 7, 8, 9, 10, 11, 12, 13, 14, to about 15 weight percent, including increments and ranges therein and there between.

Optional Additives

The compositions can also comprise at least one additive used in the cosmetics field which does not affect the properties of the compositions according to the invention, such as additives selected from fragrances, pearlescent agents, silica, proteins, protein hydrolysates, vitamins, panthenol, silicones, odor absorbers and coloring materials; essential oils; fruit extracts, for example *Pyrus* Malus (Apple) Fruit Extract, and Aloe Barbadensis Leaf Juice Powder; citric acid, sodium chloride; neutralizing or pH-adjusting agents (e.g., triethylamine (TEA) and sodium hydroxide); and combinations thereof.

Although the optional active additives are given as examples, it will be appreciated that other optional components compatible with cosmetic applications known in the art may be used. Although the optional additives are given as examples, it will be appreciated that other optional components compatible with cosmetic applications known in the art may be used.

In accordance with the various embodiments, the amount of one or more actives and additives, alone or in combination, present in the composition can be present in the composition according to the disclosure in a range from about 0.001% to about 20%, by weight, or from about 0.005% to about 0.01%, or from about 0.01% to about 0.1%, or from about 0.15% to about 5%, or from about 0.40% to about 4%, or from about 0.5% to about 2.5% by weight, or from about 1% to about 2%, or any suitable combination, sub-combination, range, or sub-range thereof by weight, based on the total weight of the composition.

Thus, any one or a combination of actives and additives may be present, by weight, based on the total weight of the composition, each one or the combination present from about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.10, 0.20, 0.30, 0.40, 0.50, 0.60, 0.70, 0.80, 0.90, 1.0, 2, 3, 4, 5, 6, 7, 8, 9, 10, 11, 12, 13, 14, 15, 16, 17, 18, 19 to about 20 weight percent, including increments and ranges therein and there between.

Substrate

In accordance with the various embodiments, provided are articles comprising a solid substrate imbued with an inventive antimicrobial system, in some embodiments in the form of a makeup removal composition. The article may be formed from synthetic materials or formed from natural biodegradable and sustainably sourced natural originated fiber, natural fiber, or regenerated or recycled natural fiber.

According to some embodiments, the substrate is a nonwoven material. A general description of nonwoven materials is given in Riedel "Nonwoven Bonding Methods and Materials", Nonwoven World (1987). These substrates are obtained according to the normal methods of the technology for the preparation of nonwoven materials. When the substrate is a nonwoven material, use may be made of a nonwoven material which does not go into ball and which is sturdy enough not to disintegrate and not to become fluffy when applied to the skin. It must be absorbent and soft at least on one side for the removal of makeup from the eyes in particular. Mention may be made, as appropriate nonwoven materials, for example, of those sold under the names Ultraloft 15285-01, Ultraloft 182-008, Ultraloft 182-010 and Ultraloft 182-016 by BBA, Vilmed M1519 Blau, Vilmed M 1550 N and 112-132-3 by Freudenberg, that sold under the name Norafin 11601-010B by Jacob Holm Industries, the flocked nonwoven materials sold under the names Univel 109 and Univel 119 by Uni Flockage and that made of viscose/PLA supplied by Sandler.

According to some embodiments comprising an article, a water insoluble substrate is employed. The water-insoluble substrate can comprise one or more layers and it can be chosen from the group consisting of woven materials, nonwoven materials, foams, sponges, waddings, as sheets, balls or films. It can in particular be a nonwoven substrate based on fibers of natural origin (flax, wool, cotton, silk, viscose, fibers made of bamboo) or synthetic origin (cellulose derivatives, polyvinyl derivatives, polyesters, such as poly(ethylene terephthalate), polyolefins, such as polyethylene (PET) or polypropylene, polyamides, such as Nylon, or acrylic derivatives) and their mixtures, such as viscose/PET, polylactic acid (PLA) or viscose/polylactic acid (viscose/PLA).

According to one embodiment, the substrate is a nonwoven material, composed of viscose or a nonwoven material composed of a viscose/microviscose mixture, through a hydro entanglement process. In some particular embodiments, the article comprises nonwoven fibers, the fibers formed from natural biodegradable and sustainably sourced fibers selected from (1) natural originated fiber comprising one or a combination of pulp, viscose, lyocell, cellulose acetate, and cotton, (2) natural fiber comprising one or a combination of hemp, flax, seaweed, ramie, banana, and pineapple, and (3) regenerated or recycled fiber comprising cotton, and combinations of these. According to one embodiment, the substrate is a nonwoven material formed of a biodegradable material, such as lyocell.

According to some embodiments, the article can comprise one or more layers having identical or different properties and having properties of elasticity and of softness and other properties appropriate to the desired use. The substrates can comprise, for example, two parts having different elasticity properties, as described in the document WO-A-99/13861, or can comprise a single layer having different densities, as described in the document WO-A-99/25318, or can comprise two layers of different textures, as described in the document WO-A-98/18441. According to some embodiments, when the article is used for the body, the article can comprise at least one rough side for making it possible, at the same time, to massage the skin or to scrub the skin.

According to the various embodiments, the article can have any size and any shape which are appropriate for the desired objective. Furthermore, it generally has a surface area of between 0.005 $m^2$ and 0.1 $m^2$, or from between 0.01 $m^2$ and 0.05 $m^2$. The weight of the substrate can be in a range between 30 gsm to 200 gsm (gram per square meter), or from between 40 gsm to 60 gsm.

According to the various embodiments, the degree of impregnation of the composition onto the substrate generally ranges from 100 to 1000%, in some embodiments from about 150% to about 700%, or from about 250% to about 400% of the weight of the substrate. The techniques for impregnating the substrates with compositions are well known and can all be applied in the present invention. Generally, the impregnating composition is heated and added to the substrate by one or more techniques comprising immersion, coating, spraying, and the like.

EXAMPLES

Example 1: Raw Materials

TABLE 1

| Raw Materials | |
|---|---|
| INCI Name | Source |
| 4-HYDROXY-ACETOPHENONE | SYMSAVE H ™; Symrise |
| [structure of 4-hydroxyacetophenone] | |
| PIROCTONE OLAMINE | OCTOPIROX ™; Clariant |
| [structure of piroctone olamine] | |

Example 2: Inventive Examples

Various representative embodiments of the inventive compositions are exemplified herein. In some instances, the composition is an antimicrobial system. In some embodiments, the composition is a makeup remover in the form of one of an O/W emulsion, a W/O emulsion, or in micellar water, in makeup removing wipes or in two-phase (or multi-phase) makeup removing compositions. In some particular exemplified embodiments, the composition is a makeup remover comprising the antimicrobial composition.

Exemplary embodiments of inventive compositions in the form of cleansing and make up removing compositions (not imbued in a substrate) according to the disclosure are provided in Table 2.

TABLE 2

| | Inventive Examples | | |
|---|---|---|---|
| Phase | INCI Name | Inventive Ex. 1 | Inventive Ex. 2 |
| A1 | WATER (QS) | 68.25 | 68.4 |
| A1 | ACRYLATES/C10-30 ALKYL ACRYLATE CROSSPOLYMER | 0.05 | 0.05 |
| A2 | GLYCERIN | 5 | 5 |
| A2 | HYDROXYACETOPHENONE | 0.5 | 0.5 |
| A2 | PIROCTONE OLAMINE | 0.2 | 0.05 |
| B | ISOHEXADECANE | 10 | 10 |
| B | ISOPROPYL MYRISTATE | 10 | 10 |
| B | DIMETHICONE | 3.5 | 3.5 |
| B | SODIUM ACRYLATES COPOLYMER (and) CAPRYLIC/CAPRIC TRIGLYCERIDE | 2.5 | 2.5 |
| | Total (Wt %): | 100 | 100 |
| | pH | 6.09 | 6.00 |
| | Viscosity (M4, 10 min) | 26.5 UD | 26.5 UD |
| | Micro Challenge Test (T0 & T2M) | PASS | PASS |
| | Eye Irritation & Discomfort | much less to none | much less to none |

Inventive Examples 1 and 2 are essentially the same composition as a commercially available product sold under the brand DERMABLEND MAKEUP DISSOLVER, except that each includes an antimicrobial system that is free (or essentially free) from phenoxyethanol and pentylene glycol, and each includes the antimicrobial 4-hydroxyacetophenone together with piroctone olamine. As reported in more detail in the context of consumer testing, the above table shows that each of the two inventive compositions are associated with little or no irritation, particularly in comparison with the comparative composition that was tested and with the overall eye irritation potential of the category of comparatives that include typical antimicrobial systems.

Example 3: Comparative Examples

Exemplary embodiments of Comparative Examples in the form of cleansing and makeup removing compositions (not imbedded in a substrate) according to the disclosure are provided in Table 3.

TABLE 3

| | Comparative Examples | | | | |
|---|---|---|---|---|---|
| Phase | INCI Name | Comparative Ex. 1 | Comparative Ex. 2 | Comparative Ex. 3 | Comparative Ex. 4 |
| A1 | WATER (QS) | 68.15 | 68.15 | 68.25 | 66.95 |
| A1 | ACRYLATES/C10-30 ALKYL ACRYLATE CROSSPOLYMER | 0.05 | 0.05 | 0.05 | 0.05 |
| A2 | GLYCERIN | 5 | 5 | 5 | 5 |
| A2 | CAPRYLYL GLYCOL | 0.3 | 0.3 | 0.3 | |
| A2 | HYDROXYACETOPHENONE | | 0.5 | | 0.5 |
| A2 | PHENOXYETHANOL | 0.5 | | 0.3 | |
| A2 | ETHYLHEXYLGLYCERIN | | | 0.1 | |
| A2 | PENTYLENEGLYCOL | | | | 1.5 |

TABLE 3-continued

| | | Comparative Examples | | | |
|---|---|---|---|---|---|
| Phase | INCI Name | Comparative Ex. 1 | Comparative Ex. 2 | Comparative Ex. 3 | Comparative Ex. 4 |
| B | ISOHEXADECANE | 10 | 10 | 10 | 10 |
| B | ISOPROPYL MYRISTATE | 10 | 10 | 10 | 10 |
| B | DIMETHICONE | 3.5 | 3.5 | 3.5 | 3.5 |
| B | SODIUM ACRYLATES COPOLYMER (and) CAPRYLIC/CAPRIC TRIGLYCERIDE | 2.5 | 2.5 | 2.5 | 2.5 |
| | Total (Wt %): | 100 | 100 | 100 | 100 |
| | pH | 6.02 | 5.86 | 5.82 | 5.82 |
| | Viscosity (M4, 10 min) | 26-36 UD | 30-35 UD | 27-30 UD | 30-35 UD |
| | Micro Challenge Test | PASS | PASS | PASS | PASS |
| | Eye Irritation & Discomfort | High | Moderate | High | Moderate |

Comparative Example 1 is a commercially available product sold under the brand DERMABLEND MAKEUP DISSOLVER and includes the antimicrobials phenoxyethanol and caprylyl glycol (representative of a typical antimicrobial system used in many cosmetics in the art as of the instant application). Comparative Example 2 is the same as Comparative Example 1 except the phenoxyethanol has been replaced by the antimicrobial 4-hydroxyacetophenone. And Comparative Example 3 is the same as Comparative Example 1 except the composition also includes the antimicrobial ethylhexylglycerine. Comparative Example 4 is the same as Comparative Example 2 except that hydroxyacetophenone was replaced with pentylene glycol. As reported in more detail in the context of consumer testing, the above table shows that each of the four comparative Examples were associated with moderate to high irritation.

Example 4: Antimicrobial Challenge Studies

Studies were conducted with each of the inventive and comparative compositions, as referenced in the tables below, to evaluate their antimicrobial efficacy against an array of microbes. The results are shown in Tables 4-11.

TABLE 4

Microbiological Study Results*: Inventive Ex. 1 at T0 & room temperature

| | Inoculum | T0/RT, CFU/g | |
|---|---|---|---|
| MICROORGANIMS | CFU/g | 7 days | 14 days |
| Escherichia coli | 1.7E+06 | <200 | <200 |
| Enterococcus faecalis | 1.1E+06 | 4.1E+04 | <200 |
| Candida albicans | 1.3E+06 | <200 | <200 |
| Aspergillus niger | 1.1E+06 | <200 | <200 |

*Limit of detection: <200 CFU/g

TABLE 5

Microbiological Study Results*: Inventive Ex. 1, after storage at 45° C. for 2 months (accelerated aging)

| | Inoculum | T2M/45° C., CFU/g | | |
|---|---|---|---|---|
| MICROORGANIMS | CFU/g | 7 days | 14 days | 28 days |
| Escherichia coli | 2.3E+06 | <200 | <200 | <200 |
| Pseudomonas aeruginosa | 2.8E+06 | <200 | <200 | <200 |
| Staphylococcus aureus | 2.5E+06 | <200 | <200 | <200 |
| Enterococcus faecalis | 1.6E+06 | 6.6E+03 | <200 | <200 |
| Candida albicans | 1.4E+06 | <200 | <200 | <200 |
| Aspergillus niger | 2.8E+06 | <200 | <200 | <200 |

*Limit of detection: <200 CFU/g

TABLE 6

Microbiological Study Results*: Inventive Ex. 2 at T0 & room temperature

| | Inoculum | T0/RT, CFU/g | |
|---|---|---|---|
| MICROORGANIMS | CFU/g | 7 days | 14 days |
| Escherichia coli | 1.7E+06 | <200 | <200 |
| Enterococcus faecalis | 1.8E+06 | 1.0E+05 | <200 |
| Candida albicans | 1.3E+06 | <200 | <200 |
| Aspergillus niger | 1.1E+06 | <200 | <200 |

*Limit of detection: <200 CFU/g

TABLE 7

Microbiological Study Results*: Inventive Ex. 2, after storage at 45° C. for 2 months (accelerated aging)

| | Inoculum | T2M/45° C., CFU/g | | |
|---|---|---|---|---|
| MICROORGANIMS | CFU/g | 7 days | 14 days | 28 days |
| Escherichia coli | 2.3E+06 | <200 | <200 | <200 |
| Pseudomonas aeruginosa | 2.8E+06 | <200 | <200 | <200 |
| Staphylococcus aureus | 2.5E+06 | <200 | <200 | <200 |
| Enterococcus faecalis | 1.6E+06 | 8.5E+04 | <200 | <200 |
| Candida albicans | 1.4E+06 | <200 | <200 | <200 |
| Aspergillus niger | 2.8E+06 | <200 | <200 | <200 |

*Limit of detection: <200 CFU/g

TABLE 8

Microbiological Study Results*: Comparative Ex. 1, at T0 & room temperature

| MICROORGANIMS | Inoculum CFU/g | T0/RT, CFU/g 7 days | 14 days |
|---|---|---|---|
| Escherichia coli | 2.5E+06 | <200 | <200 |
| Enterococcus faecalis | 2.2E+06 | <200 | <200 |
| Candida albicans | 2.6E+06 | <200 | <200 |
| Aspergillus niger | 2.9E+06 | <200 | <200 |

*Limit of detection: <200 CFU/g

TABLE 9

Microbiological Study Results*: Comparative Ex. 1, after storage at 45° C. for 2 months (accelerated aging)

| MICROORGANIMS | Inoculum CFU/g | T2M/45° C., CFU/g 7 days | 14 days | 28 days |
|---|---|---|---|---|
| Escherichia coli | 1.8E+06 | <200 | <200 | <200 |
| Pseudomonas aeruginosa | 1.9E+06 | <200 | <200 | <200 |
| Staphylococcus aureus | 1.6E+06 | <200 | <200 | <200 |
| Enterococcus faecalis | 1.6E+06 | 1.8E+03 | <200 | <200 |
| Candida albicans | 1.9E+06 | <200 | <200 | <200 |
| Aspergillus niger | 9.2E+05 | <200 | <200 | <200 |

*Limit of detection: <200 CFU/g

TABLE 10

Microbiological Study Results*: Comparative Ex. 4 at T0 & room temperature

| MICROORGANIMS | Inoculum CFU/g | T0/RT, CFU/g 7 days | 14 days |
|---|---|---|---|
| Escherichia coli | 2.4E+06 | <200 | <200 |
| Pseudomonas aeruginosa | 2.5E+06 | <200 | <200 |
| Staphylococcus aureus | 2.5E+06 | <200 | <200 |
| Enterococcus faecalis | 1.1E+06 | 3.9E+04 | <200 |
| Candida albicans | 2.4E+06 | <200 | <200 |
| Aspergillus niger | 1.4E+06 | <200 | <200 |

*Limit of detection: <200 CFU/g

TABLE 11

Microbiological Study Results Comparative Ex. 4, after storage at 45° C. for 2 months (accelerated aging)

| MICROORGANIMS | Inoculum CFU/g | T2M/45° C., CFU/g 7 days | 14 days | 28 days |
|---|---|---|---|---|
| Escherichia coli | 2.2E+06 | <200 | <200 | <200 |
| Pseudomonas aeruginosa | 2.6E+06 | <200 | <200 | <200 |
| Staphylococcus aureus | 1.8E+06 | <200 | <200 | <200 |
| Enterococcus faecalis | 1.3E+06 | 5.9E+04 | <200 | <200 |
| Candida albicans | 1.8E+06 | <200 | <200 | <200 |
| Aspergillus niger | 1.8E+06 | <200 | <200 | <200 |

*Limit of detection: <200 CFU/g

Example 5: Consumer Study of Eye Irritation and Makeup Removal (MUR) Efficacy

A consumer study was conducted to evaluate the eye irritation and/or discomfort and MUR efficacy of inventive and comparative compositions. A cohort of 10 consumers was provided with samples of each of Inventive Example 1 Comparative Ex 1 and Comparative Ex 4. The consumers used the product daily over a two-week period, and after two-weeks of usage, participated in the survey. The eye irritation/discomfort and MUR efficacy were reported using a rating scale of 1-5, as follows:

Eye Irritation/Discomfort. Scale 1-5: 1=no stinging, no discomfort; 5=very stinging & uncomfortable MUR Efficacy. Scale 1-5: 1=no removal or difficult removal; 5=complete removal with ease Results showing the generally comparable (with respect to MUR efficacy) and superior performance (with respect to eye irritation) of the inventive compositions as compared with a comparative composition are shown in Table 12. (NOTE where indicated, a subject *stopped using the Comparative Composition 1 after 1 application due to eye stinging).

TABLE 12

Raw Scores from Consumer Testing

| | Eye Irritation or Discomfort | | | MUR Efficacy | | |
|---|---|---|---|---|---|---|
| Panelist | Inventive Ex 1 | Comparative Ex 1 | Comparative Ex 4 | Inventive Ex 1 | Comparative Ex 1 | Comparative Ex 4 |
| 1 | 1 | 5 | 1 | 4.5 | 4 | 4.5 |
| 2 | 1 | 4 | 1 | 3 | 5 | 5 |
| 3 | 2 | 4 | 3 | 3 | 4 | 5 |
| 4 | 3 | 4 | 1 | 4 | 3 | 5 |
| 5* | 1 | 4 | 1 | 4 | 1 | 3 |
| 6 | 2 | 3 | 4 | 4 | 3 | 2 |
| 7 | 3 | 5 | 4 | 2 | 2 | 2 |
| 8 | 0.5 | 4 | 1.5 | 4.5 | 4 | 4.5 |
| 9 | 1 | 2 | 1 | 5 | 5 | 5 |
| 10 | 1 | 5 | 2 | 5 | 5 | 5 |
| Average | 1.55 | 4.00 | 1.95 | 3.90 | 3.60 | 4.10 |
| STD | 0.90 | 0.94 | 1.26 | 0.97 | 1.35 | 1.26 |

Example 6: Inventive and Comparative Examples for Makeup Removing Wipe Products

Table 13 shows the MUR juice formulas of inventive and Comparative Examples, eye irritation and MUR tests of the corresponding MUR wipes. All wipes were prepared by impregnating juice formula at 320% soak rate on lyocell nonwoven substrate. The results clearly demonstrated the significantly reduced eye irritation and superior micro challenge results of Inventive Ex 3 compared to the Comparative Examples.

TABLE 13

Comparison of Inventive Example v. Comparative Examples for MUR Wipes

| Phase | INCI Name | Inventive Ex. 3 Wt % | Comparative Ex. 5 Wt % | Comparative Ex. 6 Wt % | Comparative Ex. 7 Wt % | Comparative Ex. 8 Wt % |
|---|---|---|---|---|---|---|
| A | WATER | 82.265 | 82.21 | 82 | 82.15 | 81.85 |
| A | CARBOMER | 0.1 | 0.1 | 0.1 | 0.1 | 0.1 |
| A | ACRYLATES/C10-30 ALKYL ACRYLATE CROSSPOLYMER | 0.04 | 0.04 | 0.05 | 0.05 | 0.05 |
| A1 | SODIUM LAUROYL LACTYLATE (and) CERAMIDE NP (and) CERAMIDE AP (and) PHYTOSPHINGOSINE (and) CHOLESTEROL (and) XANTHAN GUM (and) CARBOMER (and) CERAMIDE EOP | 0.1 | 0.1 | 0.1 | 0.1 | 0.1 |
| B | GLYCERIN | 3 | 3 | 3 | 3 | 3 |
| B | CAPRYLYL GLYCOL | 0.3 | 0.3 | 0.3 | 0.3 | 0.3 |
| B | HYDROXY-ACETOPHENONE | 0.5 | 0.5 | 0.5 | 0.5 | 0.5 |
| B | PIROCTONE OLAMINE | 0.05 | | | | |
| B | IODOPROPYNYL BUTYLCARBAMATE (10% active) | | 0.1 | | | |
| B | PHENOXYETHANOL | | | 0.3 | | 0.3 |
| B | CHLORPHENESIN | | | | 0.15 | 0.15 |
| B | HEXYLENE GLYCOL | 1 | 1 | 1 | 1 | 1 |
| B | TRISODIUM ETHYLENEDIAMINE DISUCCINATE | 0.1 | 0.1 | 0.1 | 0.1 | 0.1 |
| C | Sodium Hydroxide | 0.045 | 0.05 | 0.05 | 0.05 | 0.05 |
| C | WATER | 0.5 | 0.5 | 0.5 | 0.5 | 0.5 |
| D | ISOHEXADECANE | 5 | 5 | 5 | 5 | 5 |
| D | ISOPROPYL MYRISTATE | 5 | 5 | 5 | 5 | 5 |
| D | DICAPRYLYL ETHER | 1 | 1 | 1 | 1 | 1 |
| D | PEG-7 Glyceryl Cocoate | 1 | 1 | 1 | 1 | 1 |
| | Total (%): | 100 | 100 | 100 | 100 | 100 |
| | pH | 6.90 | 6.84 | 6.80 | 6.77 | 6.80 |
| | Eye Irritation & Discomfort | Minimal | Minimal | Moderate | Moderate | Severe |
| | Micro Challenge Test on Wet Wipes | PASS | FAIL (*E. faecalis*) | PASS | PASS | PASS |

While the disclosure has been described with reference to a preferred embodiment, it will be understood by those skilled in the art that various changes may be made and equivalents may be substituted for elements thereof without departing from the scope of the disclosure. In addition, many modifications may be made to adapt a particular situation or material to the teachings of the disclosure without departing from the essential scope thereof. Therefore, it is intended that the disclosure not be limited to the particular embodiment disclosed as the best mode contemplated for carrying out this disclosure, but that the disclosure will include all embodiments falling within the scope of the appended claims.

The articles "a" and "an," as used herein, mean one or more when applied to any feature in embodiments of the present disclosure described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used. The adjective "any" means one, some, or all indiscriminately of whatever quantity.

"At least one," as used herein, means one or more and thus includes individual components as well as mixtures/combinations.

The transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinarily associated with the specified material(s). The term "consisting essentially of" limits the scope of a claim to the specified elements, steps or material(s) and those that do not materially affect the basic and novel characteristic(s) of the claimed disclosure. All materials and methods described herein that embody the present disclosure can, in alternate embodiments, be more specifically defined by any of the transitional terms "comprising," "consisting essentially of," and "consisting of."

The terms "free" and "devoid" indicates that no reliably measurable excluded material is present in the composition, typically 0% by weight, based on the total weight of the composition. The term "essentially free" means that, while it prefers that no excluded material is present in the composition, it is possible to have very small amounts of the excluded material in the composition of the invention, provided that these amounts do not materially affect the advantageous properties of the composition. In particular, "essentially free" means that excluded material can be present in the composition at an amount of less than about 0.1% by weight, based on the total weight of the composition.

Other than in the operating examples, or where otherwise indicated, all numbers expressing quantities of ingredients and/or reaction conditions are to be understood as being modified in all instances by the term "about," meaning within 10% of the indicated number (e.g. "about 10%" means 9%-11% and "about 2%" means 1.8%-2.2%).

All percentages and ratios are calculated by weight unless otherwise indicated. All percentages are calculated based on the total composition unless otherwise indicated. Generally, unless otherwise expressly stated herein, "weight" or "amount" as used herein with respect to the percent amount of an ingredient refers to the amount of the raw material comprising the ingredient, wherein the raw material may be described herein to comprise less than and up to 100% activity of the ingredient. Therefore, weight percent of an active in a composition is represented as the amount of raw material containing the active that is used, and may or may not reflect the final percentage of the active, wherein the final percentage of the active is dependent on the weight percent of active in the raw material.

All ranges and amounts given herein are intended to include subranges and amounts using any disclosed point as an end point. Thus, a range of "1% to 10%, such as 2% to 8%, such as 3% to 5%," is intended to encompass ranges of "1% to 8%," "1% to 5%," "2% to 10%," and so on. All numbers, amounts, ranges, etc., are intended to be modified by the term "about," whether or not so expressly stated. Similarly, a range given of "about 1% to 10%" is intended to have the term "about" modifying both the 1% and the 10% endpoints. Further, it is understood that when an amount of a component is given, it is intended to signify the amount of the active material unless otherwise specifically stated.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements. The example that follows serves to illustrate embodiments of the present disclosure without, however, being limiting in nature.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

What is claimed is:

1. A cosmetic composition, comprising:
   i. an antimicrobial agent comprising 4-hydroxyacetophenone present from about 0.2% to about 1% by weight of the composition;
   ii. at least one additional antimicrobial agent comprising piroctone olamine present from about 0.05% to about 1.5% by weight of the composition;
   iii. isohexadecane present from about 3% to about 7% by weight of the composition;
   iv. isopropyl myristate present from about 3% to about 7% by weight of the composition;
   v. dicaprylyl ether present from about 1% to about 2% by weight of the composition;
   vi. glycerin present from about 1% to about 5% by weight of the composition;
   vii. hexylene glycol present from about 1% to about 2% by weight of the composition;
   viii. acrylates/C10-30 alkyl acrylate crosspolymer present from about 0.01% to about 0.1% by weight of the composition; and
   ix. a balance of water,
   wherein the composition is free or essentially free of salicylic acid, surfactants, and antimicrobials that comprise any one or more of pentylene glycol, phenoxyethanol, hexyl glycerin, ethylhexylglycerin, octylglycerin, benzylglycerin, 3-heptoyl-2,2-propandiol, and 1,2-hexandiol,
wherein the composition imparts reduced eye irritation relative to an otherwise identical comparative composition having one or more of the pentylene glycol, the phenoxyethanol, the hexyl glycerin, the ethylhexylglycerin, the octylglycerin, the benzylglycerin, the 3-heptoyl-2,2-propandiol, or the 1,2-hexandiol in lieu of the piroctone olamine; and
wherein the cosmetic composition is a makeup removing composition.

2. The cosmetic composition according to claim 1, wherein the cosmetic composition is one of an oil-in-water emulsion, a water-in-oil emulsion, a micellar water, and a multi-phase composition.

3. The cosmetic composition according to claim 1, wherein the at least one additional antimicrobial agent further comprises one or more of the antimicrobial agents selected from caprylhydroxamic acid, chlorphenesin, benzoic acid, benzyl alcohol, phenethyl alcohol, benzalkonium chloride, salts thereof, and combinations thereof.

4. The cosmetic composition according to claim 1, wherein the composition is further free or essentially free of any one or more of parabens, ethanol, formaldehyde, and formaldehyde-derived compounds.

5. The cosmetic composition according to claim 1, wherein the composition is further free or essentially free of parabens, formaldehyde, and formaldehyde-derived compounds.

6. The cosmetic composition according to claim 1, wherein the composition is further free or essentially free of alcohols comprising one or more of ethanol and isopropyl alcohol.

7. A makeup removal composition, comprising:
  i. an antimicrobial agent comprising 4-hydroxyacetophenone present from about 0.2% to about 1% by weight of the composition;
  ii. at least one additional antimicrobial agent comprising piroctone olamine present from about 0.05% to about 1.5% by weight of the composition;
  iii. at least one lipophilic emollient is selected from the group consisting of isohexadecane, C15-19 alkane, isododecane, undecane, tridecane, isopropyl myristate, dicaprylyl ether, ethylhexyl palmitate, isopropyl palmitate, cetearyl ethylhexanoate, isononyl isononanoate, isopropyl isostearate, diisopropyl sebacate, coco caprylate/caprate, diisopropyl adipate, dimethicone, cyclopentasiloxane, and combinations thereof present from about 1% to about 12% by weight of the composition;
  iv. at least one thickener selected from the group consisting of acrylates/C10-30 alkyl acrylate crosspolymer, sodium acrylates copolymer, carbomer, xanthan gum, hydroxypropyl guar, ceratonia siliqua gum, ammonium polyacryloyldimethyl taurate, ammonium acryloyldimethyltaurate/steareth-25 methacrylate crosspolymer, polyacrylate crosspolymer-6, and combinations thereof present from about 0.01% to about 3% by weight of the composition;
  v. at least one humectant selected from the group consisting of glycerin, glycerol, butylene glycol, propylene glycol, isoprene glycol, dipropylene glycol, hexylene glycol, polyethylene glycols, monoethylene glycol, diethylene glycol, triethylene glycol, diethylene glycol, hexylene glycol, glycol ethers, monopropylene glycol glycol alkyl(C1-C4)ethers, dipropylene glycol alkyl (C1-C4)ethers, tripropylene glycol alkyl(C1-C4)ethers, squalane, triacetin, sugars, glucose, xylitol, maltitol, sorbitol, sucrose pentaerythritol, inositol, pyrrolidone carboxylic acid, lactic acid, lithium chloride, acetamide MEA, sodium lactate, urea, dicyanamide, hyaluronic acid, aloe vera, honey, seaweed extract, and combinations thereof present from about 1% to about 5% by weight of the composition; and
  vi. a balance of water,
wherein the composition is free or essentially free of salicylic acid, surfactants, and antimicrobials that comprise any one or more of pentylene glycol, phenoxyethanol, hexyl glycerin, ethylhexylglycerin, octylglycerin, benzylglycerin, 3-heptoyl-2,2-propandiol, and 1,2-hexandiol,
wherein the composition imparts reduced eye irritation relative to an otherwise identical comparative composition having one or more of the pentylene glycol, the phenoxyethanol, the hexyl glycerin, the ethylhexylglycerin, the octylglycerin, the benzylglycerin, the 3-heptoyl-2,2-propandiol, or the 1,2-hexandiol in lieu of the piroctone olamine, and
wherein the composition is formulated for the removal of makeup from skin.

8. The makeup removal composition according to claim 7, wherein the at least one or more humectant comprises the glycerin.

9. The makeup removal composition according to claim 7, further comprising: one or more additives selected from the group consisting of fragrances, pearlescent agents, silica, proteins, protein hydrolysates, vitamins, panthenol, silicones, odor absorbers, coloring materials, essential oils, fruit extracts, citric acid, sodium chloride, neutralizing agents, and combinations thereof.

10. A makeup removal and cleansing article, comprising:
  a. a water-insoluble substrate comprising a cosmetic wipe;
  b. impregnated in the water-insoluble substrate a cosmetic composition comprising:
    i. an antimicrobial agent comprising 4-hydroxyacetophenone present from about 0.2% to about 1% by weight of the composition;
    ii. at least one additional antimicrobial agent comprising piroctone olamine present from about 0.05% to about 1.5% by weight of the composition;
    iii. isohexadecane present from about 3% to about 7% by weight of the composition;
    iv. isopropyl myristate present from about 3% to about 7% by weight of the composition;
    v. dicaprylyl ether present from about 1% to about 2% by weight of the composition;
    vi. glycerin present from about 1% to about 5% by weight of the composition;
    vii. hexylene glycol present from about 1% to about 2% by weight of the composition;
    viii. acrylates/C10-30 alkyl acrylate crosspolymer present from about 0.01% to about 0.1% by weight of the composition; and
    ix. a balance of water,
wherein the composition is free or essentially free of salicylic acid, and antimicrobials that comprise any one or more of pentylene glycol, phenoxyethanol, hexyl glycerin, ethylhexylglycerin, octylglycerin, benzylglycerin, 3-heptoyl-2,2-propandiol, and 1,2-hexandiol, and
wherein the composition imparts reduced eye irritation relative to an otherwise identical comparative composition having one or more of the pentylene glycol, the phenoxyethanol, the hexyl glycerin, the ethylhexylglycerin, the octylglycerin, the benzylglycerin, the 3-heptoyl-2,2-propandiol, or the 1,2-hexanediol in lieu of the piroctone olamine.

11. The makeup removal and cleansing article according to claim 10, wherein the cosmetic composition is impregnated onto the water-insoluble substrate in a soaking rate of 250% to 400% by weight of the cosmetic composition to the weight of the substrate.

12. The makeup removal and cleansing article according to claim 10, wherein the article is a cosmetic removal wipe that comprises nonwoven fibers, the fibers formed from natural biodegradable and sustainably sourced fibers selected from the group consisting of:
   (1) natural originated fiber comprising a fiber selected from the group consisting of pulp, viscose, lyocell, cellulose acetate, cotton, and combinations thereof;
   (2) natural fiber comprising a fiber selected from the group consisting of hemp, flax, seaweed, ramie, banana, pineapple, and combinations thereof;
   (3) regenerated or recycled fiber comprising cotton; and
   (4) combinations of these.

13. A cosmetic composition, comprising:
   i. an antimicrobial agent comprising 4-hydroxyacetophenone present from about 0.2% to about 1% by weight of the composition; and
   ii. at least one additional antimicrobial agent comprising piroctone olamine present from about 0.05% to about 1.5% by weight of the composition;
   iii. isohexadecane present from about 3% to about 7% by weight of the composition;
   iv. isopropyl myristate present from about 3% to about 7% by weight of the composition;
   v. dicaprylyl ether present from about 1% to about 2% by weight of the composition;
   vi. glycerin present from about 1% to about 5% by weight of the composition;
   vii. hexylene glycol present from about 1% to about 2% by weight of the composition;
   viii. acrylates/C10-30 alkyl acrylate crosspolymer present from about 0.01% to about 0.1% by weight of the composition; and
   ix. a balance of water,
   wherein the composition is in a form selected from a bi-phase water-based cleansing system, a multi-phase water-based cleansing system, a single-phased micellar water water-based cleansing system; and a topical composition that is one of a serum, essence, cream or mask,
   wherein the composition is free or essentially free of salicylic acid, surfactants, and antimicrobials that comprise any one or more of pentylene glycol, phenoxyethanol, hexyl glycerin, ethylhexylglycerin, octylglycerin, benzylglycerin, 3-heptoyl-2,2-propandiol, and 1,2-hexanediol,
   wherein the composition imparts reduced eye irritation relative to an otherwise identical comparative composition having one or more of the pentylene glycol, the phenoxyethanol, the hexyl glycerin, the ethylhexylglycerin, the octylglycerin, the benzylglycerin, the 3-heptoyl-2,2-propandiol, or the 1,2-hexanediol in lieu of the piroctone olamine, and
   wherein the cosmetic composition is a makeup removing composition.

14. The cosmetic composition accordingly to claim 1, wherein the composition is free of surfactants.

15. The cosmetic composition of claim 1, further including:
   x. sodium hydroxide present from about 0.01% to about 0.1% by weight of the composition
   xi. caprylyl glycol present at about 0.3% by weight of the composition;
   xii. trisodium ethylenediamine disuccinate present from about 0.01% to about 0.2% by weight of the composition;
   xiii. PEG-7 glyceryl cocoate present from about 0.1% to about 2% by weight of the composition;
   xiv. sodium lauroyl lactylate, ceramide NP, ceramide AP, phytosphingosine, cholesterol, xanthan gum, carbomer, ceramide EOP cumulatively present from about 0.01% to about 0.2% by weight of the composition; and xv. carbomer present from about 0.01% to about 0.2% by weight of the composition.

16. The makeup removal composition according to claim 7, further including:
   vii. at least one further antimicrobial agent selected from the group consisting of caprylyl glycol, caprylhydroxamic acid, chlorphenesin, benzoic acid, salicylic acid, benzyl alcohol, phenethyl alcohol, benzalkonium chloride, and combinations thereof;
   viii. at least one pH-adjusting agent selected from the group consisting of sodium hydroxide, triethylamine, and combinations thereof;
   ix. trisodium ethylenediamine disuccinate;
   x. PEG-7 glyceryl cocoate; and
   xi. sodium lauroyl lactylate, ceramide NP, ceramide AP, phytosphingosine, cholesterol, xanthan gum, carbomer, ceramide EOP.

17. The makeup removal composition according to claim 16, wherein:
   the at least one further antimicrobial agent includes caprylyl glycol present at about 0.3% by weight of the composition;
   the at least one pH-adjusting agent includes sodium hydroxide present from about 0.01% to about 0.1% by weight of the composition;
   the trisodium ethylenediamine disuccinate is present from about 0.01% to about 0.2% by weight of the composition;
   the PEG-7 glyceryl cocoate is present from about 0.1% to about 2% by weight of the composition; and
   the sodium lauroyl lactylate, ceramide NP, ceramide AP, phytosphingosine, cholesterol, xanthan gum, carbomer, ceramide EOP is cumulatively present from about 0.01% to about 0.2% by weight of the composition.

18. The makeup removal composition according to claim 7, wherein the at least one lipophilic emollient includes:
   isohexadecane present from about 3% to about 7% by weight of the composition;
   isopropyl myristate present from about 3% to about 7% by weight of the composition; and
   dicaprylyl ether present from about 1% to about 2% by weight of the composition.

19. The makeup removal composition according to claim 7, wherein the at least one thickener includes acrylates/C10-30 alkyl acrylate crosspolymer present from about 0.01% to about 0.1% by weight of the composition and carbomer present from about 0.01% to about 0.2% by weight of the composition.

20. The makeup removal composition according to claim 7, wherein the at least one humectant includes glycerin present from about 1% to about 5% by weight of the composition and hexylene glycol present from about 1% to about 2% by weight of the composition.

\* \* \* \* \*